United States Patent
Heikkilä et al.

(12) 
(10) Patent No.: US 6,229,454 B1
(45) Date of Patent: May 8, 2001

(54) TELEMETRIC MEASURING METHOD AND SYSTEM

(75) Inventors: Ilkka Heikkilä; Urpo Niemelä, both of Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 08/948,744

(22) Filed: Oct. 10, 1997

(30) Foreign Application Priority Data

Oct. 11, 1996 (FI) .......................................................... 964103

(51) Int. Cl.$^7$ .................................................... G08B 13/00
(52) U.S. Cl. ............... 340/870.14; 340/539; 340/870.11; 600/508; 607/32
(58) Field of Search ........................... 340/870.11, 870.14, 340/870.16, 870.19, 870.2, 870.22, 870.24, 870.25, 539; 600/483; 607/32; 128/903

(56) References Cited

U.S. PATENT DOCUMENTS

| | | | |
|---|---|---|---|
| 3,962,697 | * 6/1976 | Vreeland | 340/870.14 |
| 4,257,038 | * 3/1981 | Rounds | 340/539 |
| 4,513,403 | 4/1985 | Troy | 607/32 |
| 4,625,733 | * 12/1986 | Saynajakangas | 600/500 |
| 4,668,950 | * 5/1987 | Russell | 340/825.65 |
| 4,748,446 | * 5/1988 | Hayworth | 340/825.64 |
| 4,958,645 | * 9/1990 | Cadell | 600/484 |
| 5,036,869 | * 8/1991 | Inhara | 600/481 |
| 5,127,404 | * 7/1992 | Wyborny | 607/32 |
| 5,137,022 | * 8/1992 | Henry | 607/32 |
| 5,241,961 | * 9/1993 | Henry | 607/32 |
| 5,354,319 | 10/1994 | Wyborny et al. | 367/83 |
| 5,400,794 | * 3/1995 | Gorman | 600/508 |
| 5,435,315 | * 7/1995 | McPhee | 600/483 |
| 5,611,346 | * 3/1997 | Heikkila | 600/509 |
| 5,632,279 | * 5/1997 | Heikkila | 600/508 |

FOREIGN PATENT DOCUMENTS

| | | |
|---|---|---|
| 0 402 620 | 12/1990 | (EP) . |
| WO 95/05578 | 2/1995 | (WO) . |
| WO 95/12350 | 5/1995 | (WO) . |

\* cited by examiner

*Primary Examiner*—Michael Horabik
*Assistant Examiner*—Albert K. Wong
(74) *Attorney, Agent, or Firm*—Hoffmann & Baron, LLP (57) ABSTRACT

The invention relates to a telemetric measuring method and system. In the method, different sensors are used to measure at least two different variables, i.e. heartbeat, the speed and pedalling cadence of a bicycle. The measurement data on each measured variable is transferred by means of telemetric data transmission to the same receiver unit. The invention is characterized in that in the telemetric data transmission to the receiver unit, the transmission pulse groups included in the measurement data on a single measure variable comprise, in the transmission pulse group, at least two intervals. The intervals are formed between at least three identifier pulses, the combination of which is specific to the particular measure variable. In order to identify the measurement data of the different measured variables, the interval combination of the transmission pulse group of the measured variable concerned is preferably different from the interval combinations appearing in the pulse groups or the pulse group sequences of the other measured variables.

28 Claims, 4 Drawing Sheets

FIG. 5

TELEMETRIC MEASURING METHOD AND SYSTEM

BACKGROUND OF THE INVENTION

1. Field of the Invention

The present invention relates to a telemetric measuring method, in which method two or more different variables are measured by different sensors, and the measurement data on each measured variable is transferred by means of telemetric data transmission to the same receiver unit.

The invention also relates to a telemetric measuring method, in which method at least two different variables, i.e. heartbeat, the speed and/or pedalling cadence of a bicycle, are measured by different sensors, and the measurement data on each measured variable is transferred by means of telemetric data transmission to the same receiver unit.

The invention also relates to a telemetric measuring method, in which method at least two different variables, i.e. heartbeat, the speed and/or operating cadence, such as paddling or rowing cadence, of a watercraft, such as a canoe, a surf board or a boat, are measured by different sensors, and the measurement data on each measured variable is transferred by means of telemetric data transmission to the same receiver unit.

The invention also relates to a telemetric measuring method, in which method at least two of the following variables are measured by different sensors: heartbeat, blood pressure, temperature, blood glucose content, blood oxygen content, and the measurement data on each measured variable is transferred by means of telemetric data transmission to the same receiver unit.

The invention also relates to a telemetric measuring system comprising one or more telemetric transmitter units, a least two different sensors in complete or partial connection with said one or more transmitter units for measuring at least two different variables, the system further comprising one telemetric receiver unit to which the measurement results measured by the different sensors can be sent telemetrically by said one or more transmitter units.

The method can be applied to a personal telemetry measuring device, e.g. a pulse meter.

2. Description of the Prior Art

Telemetric measuring methods are used e.g. for measuring a person's heartbeat. Equipment solutions are often such that the unit for measuring and transmitting the heartbeat data is arranged around the person's chest as a transmitter belt, from which the measurement data is transferred telemetrically by means of inductive coupling to a receiver unit, often implemented as a receiver strap on a person's wrist. In cycling, the receiver unit may be arranged e.g. at the bicycle handlebar.

The transmitters of e.g. heartbeat measuring devices typically send a burst of about 5 kHz each time they detect an ECG signal. The transmitter circuit of the transmitter unit consists of a resonance circuit, activated controlled by the heartbeat. The receiver unit calculates the pulse frequency, i.e. the heart rate, on the basis of the time difference between successive transmitted signals, i.e. the time difference of the bursts, the information to be transmitted, i.e. the pulse frequency or heart rate, being included in the transmission coded in the interval between the pulses. In case of a solution is used in which a group of two or more pulses is sent at each heartbeat, the pulse frequency, i.e. heart rate, can be coded inside the pulse group in the length of the interval between the pulses, but in this solution the technical implementation is more complex than usually.

When a plurality of people are using pulse measuring devices near each other, the problem that may arise is that the receiver unit may receive a pulse transmission transmitted by the transmitter unit of another person. To eliminate this drawback, it is known to use a method known from this applicant's patent publication WO 95/05578, in which a pulse group with at least two identifier pulses is used for transmitting the pulse data, the interval between the identifier pulses corresponding to the specific interval determined for each transmitter-receiver pair, the receiver unit being able to identify the transmission pulse groups addressed to it. Said method eliminates said drawbacks.

However, in present usage a need has arisen for telemetric transmission of measurement data on several different measured variables, e.g. heartbeat, pedalling speed and pedalling cadence, to the same receiver.

The characteristics of known solutions are not sufficient in the described case. In known solutions, where measurement data on several different variables is measured and received, a receiver unit may misinterpret the pulse train formed by the received measurement data on several different measured variables, leading to erroneous measurement data.

OBJECTS AND SUMMARY OF THE INVENTION

It is an object of the present invention to provide a new type of method by means of which the problems with known solutions can be avoided and a method is provided by means of which said drawbacks are eliminated and reliable disturbance-free operation is achieved when transferring the measurement data on several measured variables to a receiver.

This object is achieved with the method of the invention, characterized in that in telemetric data transmission carried out to a receiver unit the transmission pulse groups included in the measurement data on a single measured variable comprise, in the transmission pulse group, at least two intervals formed between at least three identifier pulses, the combination of said intervals being specific to that particular measured variable, whereby for identifying the measurement data on different measured variables, the interval combination of the transmission pulse group of that particular measured variable differs from the interval combinations shown by other measured variables in their specific pulse group or a pulse group sequence formed by their specific pulse groups, and that, once the receiver unit has detected an interval combination according to said at least two intervals in the pulse train it received, the transmission pulse group is identified as an transmission pulse group relating to a specific measured variable, and that a measured variable value concerning each measured variable is determined on the basis of one or more transmission pulse groups identified for the different measured variables in this manner.

The system of the invention is characterized in that, for each measured variable, the system comprises a shaping element for shaping the measured signal before telemetric transmission in such a way that on the basis of each measured signal a sequence is generated for each variable of such specific pulse groups in which a pulse group comprises at least two such intervals confined by at least three pulses that are different from the intervals of the pulse groups of other variables, and that the receiver unit comprises an identifier part for identifying each measured variable on the basis of the intervals of the pulse group, and that said identifier part is in connection with a calculation unit for calculating the values of the different measured variables.

Generally, a method having the characteristics described in the invention may be applied to a case with at least two different measured variables, but it is particularly applicable to bicycle use, the heartbeat of the cyclist, the speed and/or pedalling cadence of the bicycle being the measured variables. The invention is also applied to watercrafts, the measured variables being a person's heartbeat, the speed and operating cadence of the watercraft, such as the paddling or rowing cadence. The invention may also be applied to a case in which a noteworthy part, if not all, of the measured variables are measurements of the human body, such as two or more of the following: heartbeat, blood pressure, temperature, blood glucose content, blood oxygen content.

The method and system of the invention offer several advantages. The method and system of the invention enable telemetric transmission and reception of different measured variables to be carried out in such a way that a receiver unit can identify the pulses of the different variables in the pulse train it received, resulting in reliable operation providing correct real measurement results. The hardware configuration of the solution is also simple to implement.

BRIEF DESCRIPTION OF THE DRAWINGS

In the following, the invention will be described in more detail with reference to the accompanying drawings, in which.

DETAILED DESCRIPTION OF THE PREFERRED EMBODIMENTS

Figure 1:
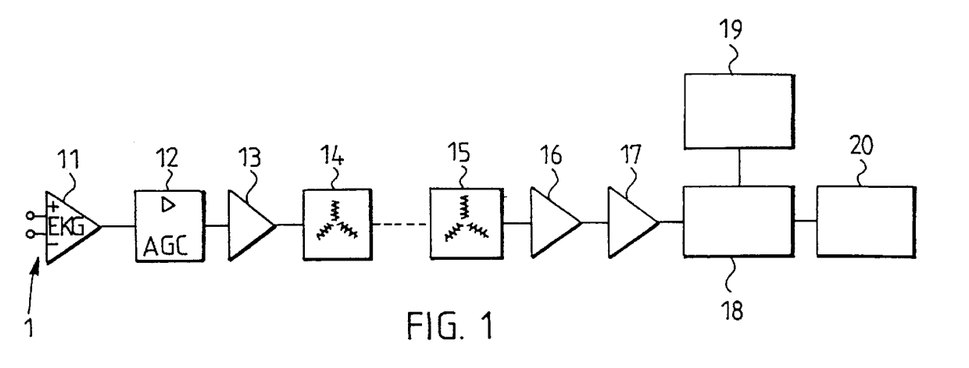
FIG. 1 is a block diagram of a conventional telemetric heartbeat measuring device, FIG. 2 schematically shows a burst signal to be fed into the magnetic coils of a transmitter unit.

FIG. 1 shows a conventional telemetric heartbeat measuring device comprising electrodes 1, an ECG preamplifier 11 with differential input terminals, an amplifier 12, e.g. an AGC amplifier, a power amplifier 13, a coil structure 14, 15, a preamplifier 16, a signal amplifier 17, a data processing unit 18, such as a microcomputer, a memory unit 19, and a display 20, such as a liquid crystal display. In FIG. 1, the electrodes 1 of the telemetric heartbeat measuring device are coupled to the differential input terminals of the ECG preamplifier. The pulse signal issued by the preamplifier 11 is amplified in the amplifier 12, e.g. an AGC amplifier, for controlling the power amplifier 13 for generating an alternating current, i.e. burst signal according to FIG. 2 for controlling the coils 14. The magnetic field detected by the receiver coils 15 is amplified in the preamplifier 16, from where the signal is led to the signal amplifier 17. The output signal of the signal amplifier 17 is processed in the data processing unit 18 which stores the pulse data, such as the heart rate, it calculated in the measuring step in the memory unit 19 and shows it on the display 20.

Figure 3:
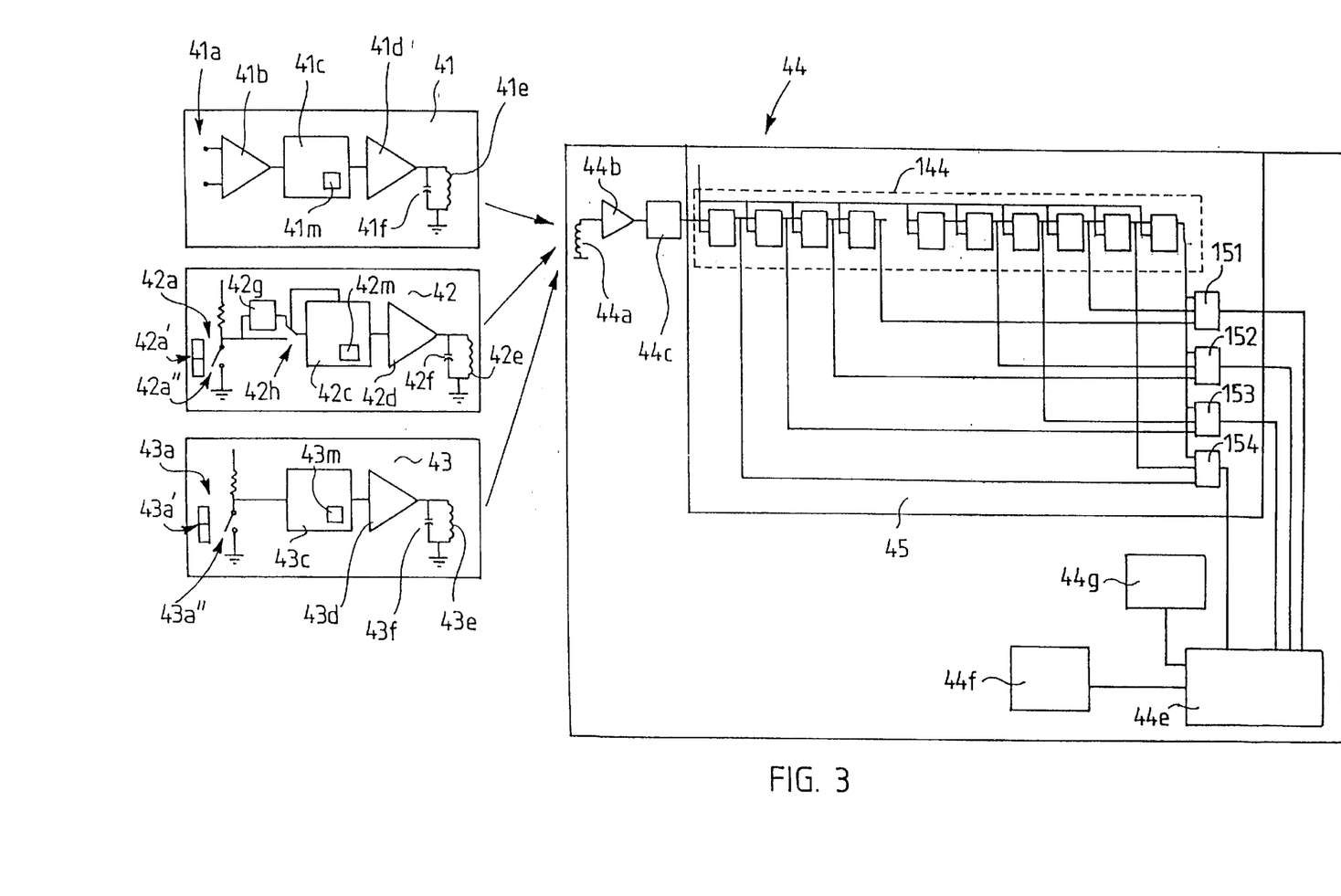
FIG. 3 shows three transmitter units and one receiver unit to be used in the method of the invention and constituting the equipment.
Figure 4:
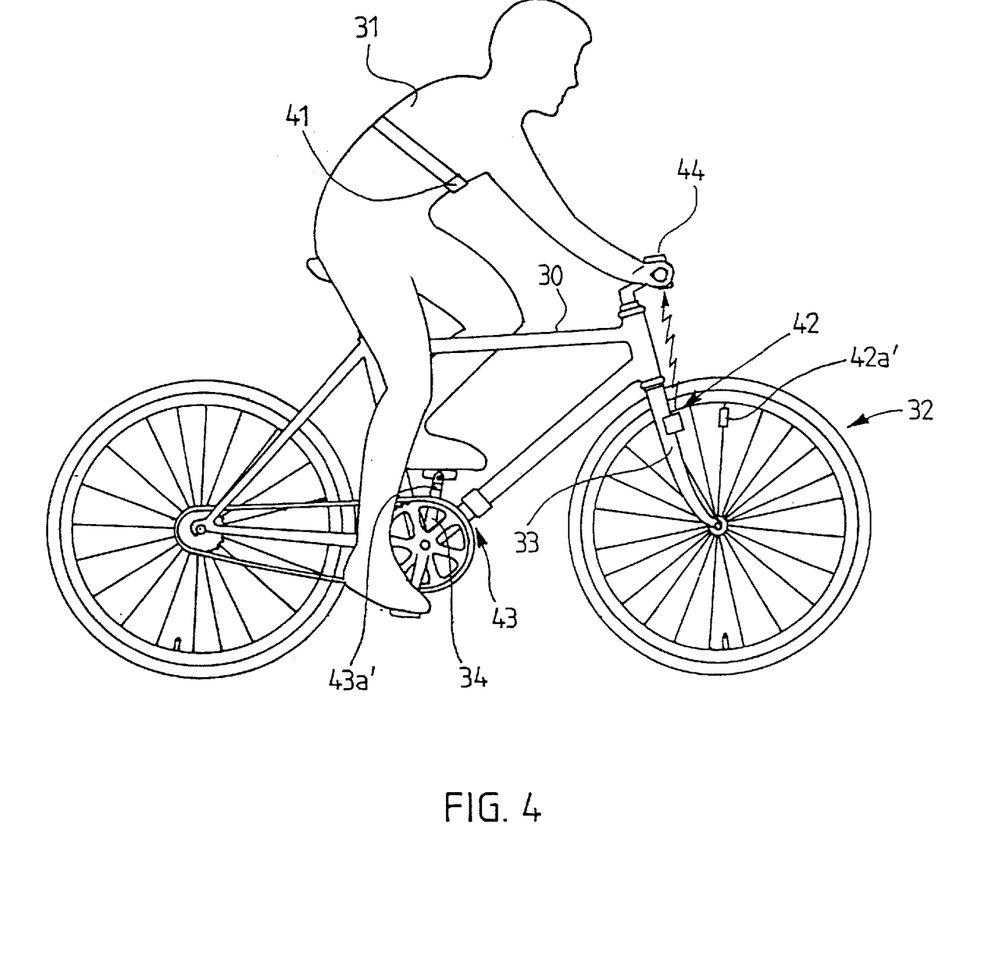
FIG. 4 shows the equipment to be used in the method of the invention applied to cycling.

FIG. 3 shows three transmitter units and one receiver unit used in the method of the invention, and in FIG. 4 an equipment comprising similar parts has been applied to cycling. Referring to FIGS. 3 and 4, the target of the application is e.g. a bicycle 30, pedalled by a person 31, e.g. a racing cyclist or a person who exercises. The equipment comprises at least two, e.g. three measuring and transmitter units 41 to 43, and a receiver unit 44 to which each measuring and transmitter unit transfers telemetrically measurement data as pulse groups shown in FIG. 5.

In FIG. 3 and 4, the first measuring and transmitter unit 41, i.e. the pulse transmitter, i.e. heart beat transmitter, is intended for measuring and transmitting the pulse. Said first measuring and transmitter unit 41 comprises a sensor 41a, such as an ECG sensor 41a, a first amplifier 41b, such as an ECG amplifier, a control unit 41c implemented by e.g. a micro circuit, a second amplifier 41d, and an oscillating resonance circuit 41e, 41f, controlled by the pulse and comprising a coil 41e and a capacitance 41f, coupled in parallel.

In FIG. 3 and 4, the second measuring and transmitter unit 42, i.e. the speed transmitter, is intended for measuring and transmitting speed, i.e. the speed of a bicycle, for instance. Said second measuring and transmitter unit 42 comprises a speed sensor 42a, a control unit 42c implemented by e.g. a micro circuit, an amplifier 42d, and an oscillating resonance circuit 42e, 42f controlled by a speed signal and comprising a coil 42e and a capacitance 42f, coupled in parallel. The speed sensor 42a may be implemented by e.g. a magnetic switch sensor 42a', 42a" in such a way that a magnet 42a' is secured to the wheel 32 of the bicycle 30, and the switch part 42a" of the sensor is e.g. in the front fork 33 of the cycle, i.e. in place, whereby the speed measurement is based on detecting the movement of the magnet 42a' past the switch part 42a" of the sensor. In a preferred embodiment the speed sensor 42 further comprises a divider, e.g. a ¼ divider 42g, which makes the sensor issue a pulse when the magnet 42a' has revolved four times past the switch part. In this way, i.e. by using the divider, high speeds can be measured (measured variable SHI in FIG. 5), whereas when the divider is not switched on, lower speeds may be measured (measured variable SLO in FIG. 5). The operation of the divider is controlled by a switch 42h.

The third measuring and transmitter unit 43 in FIGS. 3 and 4, i.e. cadence transmitter, or a transmitter indicating the pedalling cadence, is thus intended for measuring the pedalling cadence of the pedalling person 31. Said third measuring and transmitter unit 43 comprises a cadence sensor 43a, a control unit 43c implemented by e.g. a micro circuit, an amplifier 43d, and an oscillating resonance circuit 43e, 43f controlled by the cadence signal and comprising a coil 43a and a capacitance 43f, coupled in parallel. The cadence sensor 43a may be implemented by e.g. a magnetic switch sensor 43a', 43a" in such a way that a magnet 43a' is secured to the pedal of the bicycle 30 or to the crank 34 of the pedals, the switch part 43a" of the sensor and the actual transmitter unit being secured to e.g. the frame tube 35 of the bicycle 30, i.e. in place, whereby measuring the cadence, i.e. the pedalling cadence, is based on detection of the movement of the magnet 43a' past the switch part 43a" of the sensor.

Figure 5:
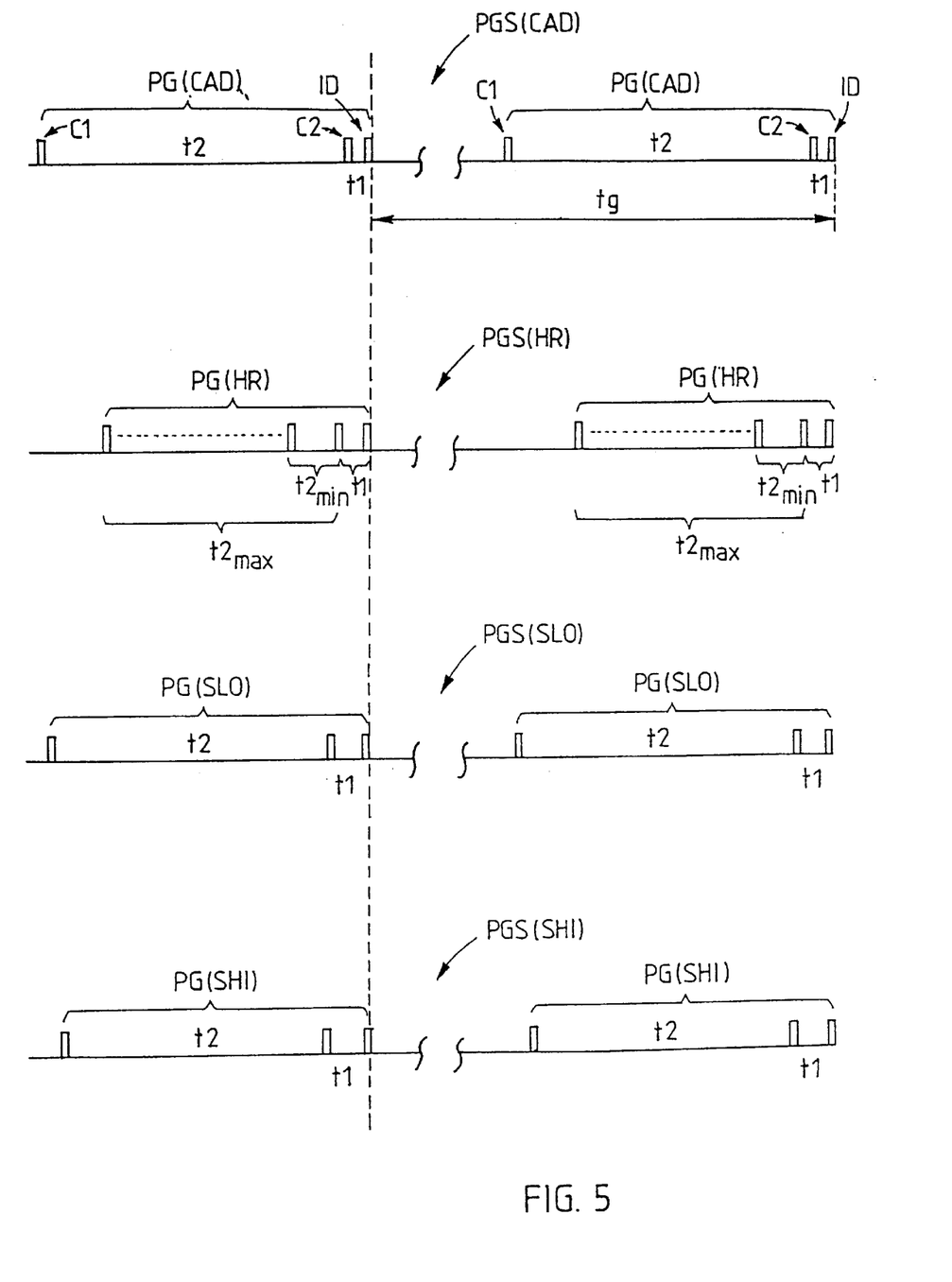
FIG. 5 shows at least 3-pulse transmission pulse groups for different measured variables, two transmission pulse groups being shown for each measured variable.

FIG. 5 shows at least 3-pulse transmission pulse groups for different measured variables, two transmission pulse groups being shown of each measured variable. The measured variables include cadence CAD, heartbeat HR, and either speed SLO or SHI depending on speed level.

Uppermost in FIG. 5 are shown two pulse groups of the pulse groups PG (CAD) of cadence CAD, i.e. the pedalling cadence. One pulse group is generated per one impulse of the sensor 43a measuring the cadence. Several successive cadence pulse groups form the pulse group sequence PGS (CAD) of the cadence.

The part of FIG. 5 next to the uppermost shows two pulse groups of the pulse groups PG(HR) of heartbeat HR. One pulse group is generated per one impulse of the sensor 41a measuring the heartbeat. Several successive heartbeat pulse groups form a pulse group sequence PGS(HR) of the heartbeat.

Pulse groups of speed are shown In FIG. 5 as the third and fourth from the top, i.e. the second lowest and lowest. Referring to FIG. 5, it should be mentioned, as far as speed is concerned, that two different versions have been shown for speed, i.e. the third from the top, i.e. the second lowest in FIG. 5 are two pulse groups PG(SLO) formed in a normal manner, i.e. without using the divider 42g. Under these, as the lowest, FIG. 5 shows two pulse groups PG(SHI) obtained using the divider 42g. In case of a lower speed, one pulse group SLO is generated per one impulse of the sensor 41a measuring the speed. In case of high speed, one pulse groups SHI is generated per four (depending on the divider) impulses of the sensor 42a measuring the speed. The several pulse groups PG(SLO) generated by the lower speed form a pulse group sequence PGS(SLO). The several pulse groups PG(SHI) generated by a higher speed form a pulse group sequence PGS(SHI).

It is essential to the invention that the transmission pulse groups PG(CAD) included in the measurement data on a single measured variable, e.g. cadence CAD, comprise in an transmission pulse group at least two such intervals t1, t2, formed between at least three identifier pulses, e.g. ID, C1, C2, the combination of which is typical of that particular measured variable, e.g. cadence CAD, whereby, for identification of the measurement data on different measured variables, the interval combination of the transmission pulse group of said measured variable differs from the combinations of intervals included in the specific pulse groups of other measured variables, i.e. heartbeat HR, and the speed SHI or SLO, and from the combinations of intervals included in transmission pulse group sequences formed by specific transmission pulse groups of the other measured variables, i.e. heartbeat HR, and speed SHI or SLO. Said at least two intervals t1, t2 of each measured variable should be different from said intervals present in the pulse groups of other variables or pulse group sequences formed by the pulse groups.

The system is a telemetric measuring system comprising one or more telemetric transmitter units 41 to 43, and at least two different sensors 41a to 43a in complete or partial connection with said one or more transmitter units 41 to 43 for measuring at least two different variables (HR, CAD, SHI, SLO). Thus the system additionally comprises one telemetric receiver unit 44, to which the measurement results of the different sensors can be sent telemetrically by said one or more transmitter units 41 to 43. The system is characterized in that for each measured variable the system comprises a shaping element 41m, 42m, 43m for shaping the measured signal before telemetric transmission in such a way that a sequence, e.g. PGS(CAD), of pulse groups, e.g. PG(CAD), specific for each variable is generated on the basis of each measured signal. In the sequence of the variable, each pulse group comprises at least two such intervals t1, t2, confined by at least three pulses, that differ from the intervals of the pulse groups of other variables. Similarly, the receiver unit 44 comprises an identifier part 45 by means of which the receiver identifies each measured variable based on the intervals of the pulse group. Such an identifier part 45 is in connection with a calculation unit 44e for calculating the values of different measured variables.

FIG. 4 shows that the shaping means are in connection with the transmission units. Each shaping means comprises at least two delay elements D(t1), D(t2) for forming a pulse group including the desired intervals t1, t2 on the basis of the measured signal. It is evident that the magnitudes of the delays determined by the delay elements differ one from another between the shaping units.

Figure 6:
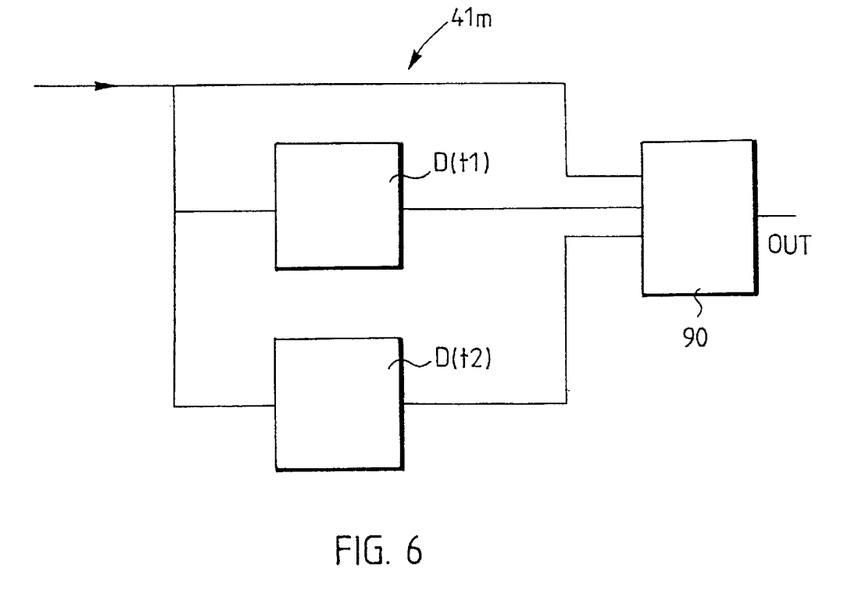
FIG. 6 is a principle diagram of a shaping means included in the transmitter unit.

The measuring and transmitter units 41 to 43 operate in such a way that on the basis of the signal given by sensor 41a, 42a,42c, respectively, the transmission pulse groups PG(HR), PG(SLO) or PH(SHI), PG(CAD), respectively, are shaped in the control unit 41c, 42c, 43c, respectively, preferably in the shaping units 41m, 42m, 43m, respectively, comprised by the control units, such that they comply with FIG. 5. FIG. 6 illustrates the operation of a shaping unit, e.g. the shaping unit 41m. In FIG. 6, the shaping unit 41m comprises delay elements D(t1) and D(t2), or an OR logic circuit 90. The measurement result of a variable is fed to all three blocks, i.e. to both delay circuits and to the OR circuit 90, the delay elements forming delays of the length t1 and t2, whereby output OUT supplies pulse groups of the type described in FIG. 5.

In FIG. 3 the receiver unit 44 comprises an inductive receiver element 44a, a signal shaping element 44b, such as an amplifier 44b, detection means 44c, an interval identifier part 45, a control unit, or calculation unit 44e, and, if needed, a memory 44f and a display 44g. The detection means 44c can be implemented e.g. as a combination of an envelope sensor and a comparator. From the point of view of the invention, the most essential block in the receiver unit 44 is the identifier part 45 which interprets the total sequence formed as the sum of the pulse groups of different variables and uses the total sequence to detect the variable concerned, and based on that the identifier part gives information to the control unit, i.e. the calculation unit 44e. The control unit, i.e. the calculation unit 44e, calculates the values of each variable based on the information received from the identifier part 45. The values of the variables may be stored in the memory 44f and/or shown on the display 44g. The identifier part 44 comprises e.g. a transfer register 144 and a plurality of collector elements 151 to 154. The transfer register comprises e.g. D flip-flops Q1 to Q38, each flip-flop operating in such a way that the flip-flop supplies to its output what it receives in its input, i.e. if the flip-flop input value is "1", it issues the state "1" as the output. The same applies to the state "0". The transfer register 144 comprises a clock control CLK for the flip-flops. The transfer register 144 is filled with received signal at a pace given by the clock CLK steps. If one of the pulse groups PG(HR), PG(SLO) or PG(SHI), PG(CAD), respectively, of FIG. 5 is present in the signal received by the receiver 44, the control unit sees it in the collector elements 151 to 154. Each variable HR, SHI, SLO, CAD has its own collector circuit.

Thus the invention relates to a telemetric measuring method in accordance with an embodiment of which three different measured variables, i.e. heartbeat, speed and pedalling cadence of a bicycle, are measured by different sensors, and the measurement data on each measured variable is transferred by telemetric data transmission to the same receiver unit 44. In the invention, telemetric data transmission to the receiver unit 44 is carried out in such a way that the transmission pulse groups included in the measurement data on a single measured variable comprise, in the transmission pulse group, at least two such intervals, formed between at least three identifier pulses, whose combination is specific to that particular measured variable, whereby, for identification of the different measured variables, the interval combination of the transmission pulse group of the measured variable concerned differs from the interval combinations that other measured variables show in their specific pulse groups or in a specific pulse group sequence formed by their pulse groups. Once the receiver unit 44 detects that an interval combination according to said at least two intervals is present in a common received pulse train, the transmission pulse group is identified as an transmission pulse group concerning a given measured variable, i.e. heartbeat, bicycle speed or pedalling cadence. A value for each measured variable, e.g. heartbeat, bicycle speed or pedalling cadence, is determined for the different measured variables, i.e. heartbeat, bicycle speed and pedalling cadence, on the basis of one or more transmission pulse groups identified in the above manner.

The solution in a preferred embodiment of the invention is such that said at least two intervals t1, t2 present in the transmission pulse group, e.g. PG(CAD), of a single measured variable, e.g. cadence CAD, have been selected in such a way that intervals of the same length do not appear in the transmission pulse groups PG(HR), PG(SLO) or PG(SHI) of the other measured variables, e.g. heartbeat HR, and speed SLO or SHI, or in the transmission pulse group sequences PGS(HR) PGS(SLO) or PGS(SHI) specific to the measured variables and formed by the transmission pulse groups of the other single measured variables, i.e. heartbeat or speed. This can be seen from FIG. 5, in which the intervals t1, t2 of the different measured variables have different lengths. According to the observations made by the applicant, a suitable length for the intervals t1 is between 10 and 50 ms. Similarly, according to the observations made by the applicant, a suitable length for the intervals t2 is between 50 and 250 ms. According to the observations of the applicant, a difference of about 5 to 20 ms is sufficient to make the lengths of the intervals of the different variables sufficiently different. The difference in length between intervals t1 and t2, in turn, is great. The difference in length between the intervals t1 of the different variables is slight. Similarly, the difference in length between the intervals t2 of the different variables is slight. The preferred embodiments ensure that the different variables are distinguished one from another.

When considering the difference in length between the intervals t2, FIG. 5 shows, however, that in some variable, i.e. heartbeat HR in the Figure, the interval t2 may be notably shorter than that of the other variables. This is due to the fact that in the preferred embodiment a user identifier code has been coded in the interval of said variable HR, i.e. the length of the interval t2 in said variable HR, i.e. heartbeat, depends on the person concerned. Said preferred embodiment increases the reliability of the measurement in a simple manner.

The solution of a preferred embodiment of the invention is such that one or more transmitter units transmit pulse groups at intervals proportional to the frequency of occurrence of a measured variable, the receiver determining the measuring result of the measured variable based on the interval between the pulse groups. The interval tg between successive pulse groups PG (CAD) of cadence CAD may serve as an example.

The solution of a preferred embodiment of the invention is such that in the method one or more transmitter units 41 to 43 transmit such pulse groups that include, in addition to the two intervals described, at least one measuring value interval whose length is proportional to the value of the measured variable, and that in this case the receiver determines the value of said measured variable based on said measuring value interval of the pulse group (not shown).

In a preferred embodiment of the invention, the lengths of the intervals t1, t2 have been selected such that the length of each interval t1, t2 is shorter than the estimated limit value, or minimum length of the interval, i.e. time period, comprising the variable to be measured, and/or longer than the maximum length of the interval comprising the value of the variable to be measured. Referring to heartbeat HR, said limit value, i.e. minimum length, is about 250 ms, corresponding to the highest imaginable pulse value 240 pulses/minute, i.e. 4 beats/second. This preferred embodiment prevents the interval comprising the measuring value (the interval tg between the pulse groups or some third interval between the pulses inside the pulse group) from disturbing the measurement.

The solution of a preferred embodiment of the invention is such that a dedicated transmitter unit 41 to 43 is used for each measured variable in transferring the measurement data on the different measured variables to the same receiver 44. This simplifies equipment implementation and the operation of the method.

In some cases it is advantageous to use a common transmitter unit for transferring the measurement data on at least two different measured variables to the same receiver. The solution of a preferred embodiment of the invention is such that a common transmitter unit is used for transferring the measurement results of heartbeat and some other variable measured from the body, especially temperature. In FIG. 4, for example, the pulse transmitter belt could comprise a sensor measuring body temperature in the same entity. Said solution reduces the number of transmitter units.

The method of the invention is implemented by transferring the measurement data on each measured variable HR, CAD, SLO (or SHI) to the receiver unit 44 in an transmission pulse group sequence specific to the measured variable and formed by successive pulse groups, and that the pulse group sequences of the different measured variables HR, CAD, SLO (or SHI) form a total sequence which is transferred to a receiver in telemetric data transmission.

The solution of a preferred embodiment of the invention is such that the measuring frequency of one or more measured variables, e.g. speed, is changed (by the divider 42g), and at the same time the combination formed by said at least two intervals t1, t2 of the transmission pulse group of the measured variable concerned is changed, and that the sensor part 45 of the receiver 44 detects the change in the combination formed by said intervals, and based on this information the receiver 44 changes the measuring value so that it corresponds to the actual measuring value, i.e. removes the influence of the divider 42g. Relating to this, the solution of a preferred embodiment of the invention is such that the measuring frequency of a measured variable, particularly speed, and the pulse group intervals are changed automatically once the measuring value exceeds a given value or falls below a given value.

The method of the invention is applied to a personal telemetry measuring device, e.g. a pulse meter.

In addition to the above cycling application, the invention is also applied to watercrafts, the measured variables being e.g. a person's heartbeat, the speed and operating cadence of the watercraft, such as the paddling or rowing cadence. In addition, the invention may be applied to a case where a significant part of the measured variables, if not all, are measurements concerning the human body, such as two or more of the following: heartbeat, blood pressure, temperature, blood glucose content, blood oxygen content.

The minimum number of measured variables is two, and they can be selected in accordance with the application and the measuring needs.

Even though the invention has been explained in the above with reference to examples in accordance with the accompanying drawings, it is obvious that the invention is not restricted to them but can be modified in a variety of ways within the scope of the inventive idea disclosed in the attached claims.

What is claimed is:

1. A telemetric measuring method, the method comprising the steps of:

measuring a value of at least one of a plurality of variables, the value of the variable being responsive to at least one of a bodily function and a bodily movement, the value of the at least one of the plurality of variables being measured by a sensor;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

2. A telemetric measuring method, the method comprising the steps of:

measuring a value of at least one of the plurality of variables, the value of the variable being responsive to at least one of a bodily function and a bodily movement, the value of the at least one of the plurality of variables being measured by a sensor, the at least one of the plurality of variables including at least one of a heartbeat rate, a bicycle speed, and a bicycle pedalling cadence;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one the plurality of variables from a duration of time between the at least two transmission pulse groups.

3. A telemetric measuring method, the method comprising the steps of:

measuring a value of at least one of the plurality of variables, the value of the variable being responsive to at least one of a bodily function and a bodily movement, the value of the at least one of the plurality of variables being measured by a sensor, the at least one of the plurality of variables including at least one of a heartbeat rate, a watercraft speed, and a watercraft operating cadence;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse group, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

4. A telemetric measuring method, the method comprising the steps of:

measuring a value of the at least one of the plurality of variables, the value of the variable being responsive to at least one of a bodily function and a bodily movement, the at least one of the plurality of variables being measured by a corresponding sensor, the at least one of the plurality of variables including at least one of a heartbeat rate, a blood pressure, a temperature, a blood glucose content, and a blood oxygen content;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

5. A telemetric measuring method as defined by claims 1, 2, 3, or 4, wherein the intervals are separated by the at least three pulses of different transmission pulse groups of the plurality of transmission pulse groups.

6. A telemetric measuring method as defined by claims 1, 2, 3, or 4, wherein a first combination of the at least two intervals is unequal to a second combination of at least two different intervals, a first variable of the plurality of variables being identifiable by the first combination, a second variable of the plurality of variables being identifiable by the second combination.

7. A telemetric measuring method as defined by claims 1, 2, 3, or 4, wherein the step of generating at least one transmission pulse group further includes the step of generating at least two transmission pulse groups separated by a duration of time proportional to the value of the at least one of the plurality of variables.

8. A telemetric measuring method as defined by claims 1, 2, 3, or 4, wherein the at least two intervals are at least one of less than the value of the plurality of variables and greater than the value of the plurality of variables.

9. A telemetric measuring method as defined by claims 1, 2, 3, or 4, wherein the at least one transmission pulse group is transmitted by a dedicated transmitter, the dedicated transmitter transmitting only transmission pulse groups being used to represent the value of the at least one of the plurality of variables.

10. A telemetric measuring method as defined by claims 1, 2, 3, or 4, wherein the at least one transmission pulse group is transmitted by a common transmitter, the common transmitter transmitting transmission pulse groups being used to represent the values of at least two of the plurality of variables.

11. A telemetric measuring method as defined by claim 10, wherein the at least one transmission pulse group is transmitted by a common transmitter, the common transmitter transmitting transmission pulse groups representative of a heartbeat rate and at least one other bodily variable.

12. A telemetric measuring method as defined by claims, 1, 2, 3, or 4, wherein the step of transmitting the at least one transmission pulse group further includes the step of transmitting at least two transmission pulse groups as a transmission pulse group sequence, the transmission pulse group sequence being representative of the at least one of the plurality of variables.

13. A telemetric measuring method as defined by claims 1, 2, 3, or 4, wherein the step of measuring the at least one of the plurality of variables further includes the step of changing a frequency at which at least one of the plurality of variables is measured, wherein the step of generating the at least two transmission pulse groups further includes the step of changing at least one of the at least two intervals in response to changing the frequency, the change in the at least one of the at least two intervals being representative of the change in the frequency of measuring, wherein the step of determining the value of the at least one of the plurality of variables further includes the steps of detecting the change in the at least one of the at least two intervals and adjusting the value of the at least one of the plurality of variables in response to the change in the at least one of the at least two intervals.

14. A telemetric measuring method as defined by claim 13, wherein the step of changing the frequency at which at least one of the plurality of variables is measured further includes the step of automatically changing the frequency at which at least one of the plurality of variables is measured in response to the value of the at least one of the plurality of variables being one of greater than and less than a first value, wherein the step of changing the at least two intervals in response to changing the frequency further includes the step of automatically changing the at least one of the at least two intervals in response to the value of the at least one of the plurality of variables being one of greater than and less than the first value.

15. A telemetric measuring method as defined by claim 13, wherein the at least one of the plurality of variables includes speed.

16. A telemetric measuring method as defined by claims 1, 2, 3, or 4, wherein the at least two intervals are successive.

17. A telemetric measuring method as defined by claims 1, 2, 3, or 4, wherein at least one of the at least two intervals is representative of an identity of a user.

18. A telemetric measuring method as defined by claim 17, wherein the at least one of the plurality of variables includes a heartbeat rate of the user.

19. A telemetric measuring method as defined by claims 1, 2, 3, or 4, wherein the method is used in a personal telemetry-measuring device.

20. A telemetric measurement system, the telemetric measurement system comprising:
   a plurality of sensors, each of the plurality of sensors measuring a value of at least one of a plurality of variables, the value of the variable being responsive to at least one of a bodily function and a bodily movement;
   a plurality of shaping circuits, each of the plurality of shaping circuits being responsive to at least one of the plurality of sensors, the plurality of shaping circuits generating at least two transmission pulse groups, the at least two transmission pulse groups being used to represent the value of the at least one of the plurality of variables, at least one of the at least two transmission pulse groups including at least two intervals and at least three pulses, the at least two intervals being separated by the at least three pulses, the at least one of the plurality of variables being identifiable by the at least two intervals;
   at least one transmitter, the at least one transmitter transmitting the at least two transmission pulse groups;
   a receiver, the receiver receiving being responsive to the at least two transmission pulse groups;
   an identifying circuit, the identifying circuit being responsive to the at least two transmission pulse groups, the identifying circuit identifying the at least one of the plurality of variables from the at least two intervals of at least one of the received at least two transmission pulse groups; and
   a calculating circuit, the calculating circuit determining the value of the at least one of the plurality of variables from a duration of time between the received at least two transmission pulse groups.

21. A telemetric measurement system as defined by claim 20, wherein the plurality of shaping circuits are coupled to the at least one transmitter.

22. A telemetric measurement system as defined by claim 20, wherein each of the plurality of shaping circuits includes at least two delay elements, the at least two delay elements generating the at least two intervals.

23. A telemetric measurement system as defined by claim 20, wherein the sensor is able to change a frequency at which at least one of the plurality of variables is measured, wherein at least one of the plurality of shaping circuits is able to change at least one of the at least two intervals in response to the change in the frequency of measuring.

24. A telemetric measurement system as defined by claim 20, wherein the identifying circuit includes a transfer register, at least one of the received at least two transmission pulse groups being inputted to the transfer register.

25. A telemetric measurement system as defined by claim 20, wherein the plurality of sensors measures a heartbeat rate and at least one of a bicycle speed and a pedalling cadence.

26. A telemetric measurement system as defined by claim 20, wherein the plurality of sensors measures a heartbeat rate and at least one of a watercraft speed and an operating cadence.

27. A telemetric measurement system as defined by claim 20, wherein the system is used in a personal telemetry-measuring device.

28. A telemetric measuring method as defined by claim 14, wherein the at least one of the plurality of variables includes speed.

\* \* \* \* \*

UNITED STATES PATENT AND TRADEMARK OFFICE
CERTIFICATE OF CORRECTION

PATENT NO.      : 6,229,454 B1
DATED           : May 8, 2001
INVENTOR(S)     : Ilkka Heikkilä et al.

It is certified that error appears in the above-identified patent and that said Letters Patent is hereby corrected as shown below:

Delete columns 1 through 14, and substitute therefor, columns 1 through 12, as shown on the attached pages.

Signed and Sealed this

First Day of April, 2003

JAMES E. ROGAN
*Director of the United States Patent and Trademark Office*

TELEMETRIC MEASURING METHOD AND SYSTEM

BACKGROUND OF THE INVENTION

1. Field of the Invention

The present invention relates to a telemetric measuring method, in which method two or more different variables are measured by different sensors, and the measurement data on each measured variable is transferred by means of telemetric data transmission to the same receiver unit.

The invention also relates to a telemetric measuring method, in which method at least two different variables, i.e. heartbeat, the speed and/or pedalling cadence of a bicycle, are measured by different sensors, and the measurement data on each measured variable is transferred by means of telemetric data transmission to the same receiver unit.

The invention also relates to a telemetric measuring method, in which method at least two different variables, i.e. heartbeat, the speed and/or operating cadence (such as paddling or rowing cadence of a watercraft, such as a canoe, a surf board or a boat) are measured by different sensors, and the measurement data on each measured variable is transferred by means of telemetric data transmission to the same receiver unit.

The invention also relates to a telemetric measuring method, in which method at least two of the following variables are measured by different sensors: heartbeat, blood pressure, temperature, blood glucose content, blood oxygen content, and the measurement data on each measured variable is transferred by means of telemetric data transmission to the same receiver unit.

The invention also relates to a telemetric measuring system comprising one or more telemetric transmitter units, at least two different sensors in complete or partial connection with one or more transmitter units for measuring at least two different variables, and one telemetric receiver unit to which the measurement results measured by the different sensors can be sent telemetrically by the one or more transmitter units.

The method can be applied to a personal telemetry measuring device, e.g. a pulse meter.

2. Description of the Prior Art

Telemetric measuring methods are used e.g. for measuring a person's heartbeat. Equipment solutions are often such that the unit for measuring and transmitting the heartbeat data is arranged around the person's chest as a transmitter belt, from which the measurement data is transferred telemetrically by means of inductive coupling to a receiver unit, often implemented as a receiver strap on a person's wrist. In cycling, the receiver unit may be located on the bicycle handlebar.

The transmitters associated with, for instance, heartbeat measuring devices typically send a burst of about 5 kHz each time they detect an ECG signal. The transmitter circuit of the transmitter unit consists of a resonance circuit controlled by the heartbeat. The receiver unit calculates the pulse frequency, i.e. the heart rate, on the basis of the time difference between successive transmitted signals (the time difference of the bursts). The information to be transmitted, i.e. the pulse frequency or heart rate, is preferably included in the transmission and coded in the interval between the pulses. If a group of two or more pulses is transmitted in response to each heartbeat, the pulse frequency, i.e. heart rate, can be coded inside the pulse group during the interval between the pulses, but in this solution the technical implementation is relatively complex.

When a plurality of people are using pulse measuring devices near each other, the problem that may arise is that the receiver unit may receive a pulse transmission transmitted by the transmitter unit of another person. To eliminate this drawback, it is known to use a method disclosed in the Applicant's patent publication WO 95/05578, in which a pulse group with at least two identifier pulses is used to transmit the pulse data. The interval between the identifier pulses corresponds to the specific interval associated with a particular transmitter-receiver pair, and the receiver unit is able to identify the transmission pulse groups addressed to it. This method eliminates the draw-backs discussed above.

However, in present usage a need has arisen for telemetric transmission of measurement data representing several different measured variables, e.g. heartbeat, pedalling speed and pedalling cadence, to the same receiver.

The characteristics of known solutions are insufficient. In known solutions, where measurement data on several different variables is measured and received, a receiver unit may misinterpret the pulse train formed by the received measurement data on several different measured variables, resulting in erroneous measurement data.

OBJECTS AND SUMMARY OF THE INVENTION

It is an object of the present invention to provide a novel method which avoids the problems and disadvantages of known solutions and provides reliable, disturbance-free operation when transferring the measurement data on several measured variables to a receiver.

This object is achieved with the method of the invention, characterized in that in telemetric data transmission transmitted to a receiver unit, the transmission pulse groups included in the measurement data on a single measured variable include, in the transmission pulse group, at least two intervals formed between at least three identifier pulses. The combination of the intervals being specific to that particular measured variable, whereby for identifying the measurement data on different measured variables, the interval combination of the transmission pulse group of that particular measured variable differs from the interval combinations shown by other measured variables in their specific pulse group or a pulse group sequence formed by their specific pulse groups. Once the receiver unit has detected an interval combination according to the at least two intervals in the pulse train it received, the transmission pulse group is identified as a transmission pulse group relating to a specific measured variable. A measured variable value concerning each measured variable is determined on the basis of one or more transmission pulse groups identified for the different measured variables in this manner.

The system of the invention is characterized in that, for each measured variable, the system includes a shaping element for shaping the measured signal before telemetric transmission such that, on the basis of each measured signal, a sequence is generated for each variable of such specific pulse groups in which a pulse group comprises at least two such intervals confined by at least three pulses that are different from the intervals of the pulse groups of other variables. The receiver unit includes an identifier part for identifying each measured variable on the basis of the intervals of the pulse group, and the identifier part is in connection with a calculation unit for calculating the values of the different measured variables.

Generally, a method having the characteristics described in the invention may be applied to a case with at least two different measured variables, but it is particularly applicable to bicycle use, the heartbeat of the cyclist, the speed and/or pedalling cadence of the bicycle being the measured variables. The present invention is also applicable to watercrafts, the measured variables being a person's heartbeat, the speed and operating cadence of the watercraft, such as paddling or rowing cadence. The invention may also be applied to a case in which a noteworthy part, if not all, of the measured variables are measurements of the human body, such as two or more of the following: heartbeat, blood pressure, temperature, blood glucose content and blood oxygen content.

The method and system of the invention offer several advantages including telemetric transmission and reception of different measured variables to be carried out in such a way that a receiver unit can identify the pulses of the different variables in the pulse train it received, resulting in reliable operation and accurate measurement results. The hardware configuration of the solution is also simple to implement.

BRIEF DESCRIPTION OF THE DRAWINGS

Figure 2:
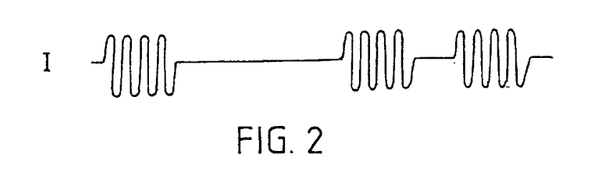

In the following, the invention will be described in more detail with reference to the accompanying drawings, in which FIG. 1 is a block diagram of a conventional telemetric heartbeat measuring device, FIG. 2 schematically shows a burst signal to be fed into magnetic coils of a transmitter unit, FIG. 3 shows three transmitter units and one receiver unit to be used in the method and system of the invention, FIG. 4 shows the equipment to be used in the method of the invention applied to cycling, FIG. 5 shows at least 3-pulse transmission pulse groups for different measured variables, two transmission pulse groups being shown for each measured variable, FIG. 6 is a block diagram of a shaping means preferably included in the transmitter unit.

DETAILED DESCRIPTION OF THE PREFERRED EMBODIMENTS

FIG. 1 shows a conventional telemetric heartbeat measuring device comprising electrodes 1, an ECG preamplifier 11 with differential input terminals, an amplifier 12, e.g. an AGC amplifier, a power amplifier 13, a coil structure 14, 15, a preamplifier 16, a signal amplifier 17, a data processing unit 18, such as a microcomputer, a memory unit 19, and a display 20, such as a liquid crystal display. In FIG. 1, the electrodes 1 of the telemetric heartbeat measuring device are coupled to the differential input terminals of the ECG preamplifier. The pulse signal issued by the preamplifier 11 is amplified in the amplifier 12, e.g. an AGC amplifier, for controlling the power amplifier 13. The power amplifier 13 generates an alternating current, i.e. burst signal according to FIG. 2 for controlling the coils 14. The magnetic field detected by the receiver coils 15 from the coils 14 is amplified in the preamplifier 16, and fed to the signal amplifier 17. The output signal of the signal amplifier 17 is processed in the data processing unit 18, which stores the pulse data, such as the heart rate, calculated in the measuring step, in the memory unit 19 and shows it on the display 20.

FIG. 3 shows three transmitter units and one receiver unit used in the method of the invention, and FIG. 4 shows a system comprising similar elements applied to cycling. Referring to FIGS. 3 and 4, the target of the application is e.g. a bicycle 30, pedalled by a person 31, e.g. a racing cyclist or a person who exercises. The equipment comprises at least two measuring and transmitter units 41 to 43, and a receiver unit 44 to which each measuring and transmitter unit telemetrically transfers measurement data as pulse groups shown in FIG. 5.

In FIGS. 3 and 4, the first measuring and transmitter unit 41, i.e. the pulse transmitter, i.e. heart beat transmitter, is intended for measuring and transmitting the pulse. Said first measuring and transmitter unit 41 comprises a sensor $41a$, such as an ECG sensor $41a$, a first amplifier $41b$, such as an ECG amplifier, a control unit $41c$ implemented by e.g. a microcontroller, a second amplifier $41d$, and an oscillating resonance circuit $41e$, $41f$, which is controlled by the pulse. The oscillating resonance circuit includes a coil $41e$ and a capacitance $41f$ coupled in parallel.

In FIGS. 3 and 4, the second measuring and transmitter unit 42, i.e. the speed transmitter, is intended for measuring and transmitting speed, i.e. the speed of a bicycle, for instance. Said second measuring and transmitter unit 42 preferably comprises a speed sensor $42a$, a control unit $42c$ preferably implemented by a microcontroller, an amplifier $42d$, and an oscillating resonance circuit controlled by a speed signal. The oscillator resonance circuit includes a coil $42e$ and a capacitance $42f$ coupled in parallel. The speed sensor $42a$ may be implemented by e.g. a magnetic switch sensor $42a'$, $42a''$ in such a way that a magnet $42a'$ is secured to the wheel 32 of the bicycle 30, and the switch part $42a''$ of the sensor is e.g. on the front fork 33 of the cycle, whereby the speed measurement is based on detecting the movement of the magnet $42a'$ past the switch part $42a''$ of the sensor. In a preferred embodiment the speed sensor 42 further comprises a divider, e.g. a ¼ divider $42g$, which makes the sensor issue a pulse when the magnet $42a'$ has revolved four times past the switch part. In this way, i.e. by using the divider, high speeds can be measured (measured variable SHI in FIG. 5), whereas when the divider is not switched on, lower speeds may be measured (measured variable SLO in FIG. 5). The operation of the divider is controlled by a switch $42h$.

The third measuring and transmitter unit 43 in FIGS. 3 and 4, i.e. a cadence transmitter, or a transmitter indicating the pedalling cadence, is thus intended for measuring the pedalling cadence of the pedalling person 31. Said third measuring and transmitter unit 43 comprises a cadence sensor $43a$, a control unit $43c$ implemented by e.g. microcontroller, an amplifier $43d$, and an oscillating resonance circuit $43e$, $43f$ controlled by the cadence signal. The oscillating resonance circuit includes a coil $43a$ and a capacitance $43f$ coupled in parallel. The cadence sensor $43a$ may be implemented by e.g. a magnetic switch sensor $43a'$, $43a''$ in such a way that a magnet $43a'$ is secured to the pedal of the bicycle 30 or to the crank 34 of the pedals, and the switch part $43a''$ of the sensor and the actual transmitter unit are secured to e.g. the frame tube 35 of the bicycle 30. Thus, the pedalling cadence is based on detection of the movement of the magnet $43a'$ past the switch part $43a''$ of the sensor.

FIG. 5 shows at least 3-pulse transmission pulse groups for different measured variables, two transmission pulse groups being shown for each measured variable. The measured variables include cadence CAD, heartbeat HR, and either speed SLO or SHI depending on speed level.

Uppermost in FIG. 5 are shown two pulse groups of the pulse groups PG (CAD) of cadence CAD, i.e. the pedalling cadence. One pulse group is generated per one impulse of the sensor $43a$ measuring the cadence. Several successive cadence pulse groups form the pulse group sequence PGS (CAD) of the cadence.

The part of FIG. 5 next to the uppermost shows two pulse groups of the pulse groups PG(HR) of heartbeat HR. One pulse group is preferably generated in response to one impulse of the sensor 41a measuring the heartbeat. Several successive heartbeat pulse groups form a pulse group sequence PGS(HR) of the heartbeat.

Pulse groups of speed are shown in FIG. 5 as the third and fourth from the top, i.e. the second lowest and lowest pulse groups. Referring to FIG. 5, it should be mentioned, as far as speed is concerned, that two different versions have been shown for speed, i.e. the third from the top, i.e. the second lowest in FIG. 5 are two pulse groups PG(SLO) formed in a normal manner, i.e. without using the divider 42g. The lowest pulse group in FIG. 5 shows two pulse groups PG(SHI) obtained using the divider 42g. In case of a lower speed, one pulse group SLO is preferably generated in response to one impulse of the sensor 41a measuring the speed. In case of high speed, one pulse group SHI is preferably generated in response to four (depending on the divider) impulses of the sensor 41a measuring the speed. The several pulse groups PG(SLO) generated by the lower speed form a pulse group sequence PGS(SLO). The several pulse groups PG(SHI) generated by a higher speed form a pulse group sequence PGS(SHI).

It is essential to the invention that the transmission pulse groups PG(CAD) included in the measurement data on a single measured variable, e.g. cadence CAD, comprise in a transmission pulse group at least two such intervals t1, t2, formed between at least three identifier pulses, e.g. ID, C1, C2. The combination of identifier pulses identify a particular measured variable, e.g. cadence CAD. The interval combination of the transmission pulse group of said measured variable differs from the combinations of intervals included in the specific pulse groups of other measured variables, i.e. heartbeat HR, and the speed SHI or SLO, and from the combinations of intervals included in transmission pulse group sequences formed by specific transmission pulse groups of the other measured variables, i.e. heartbeat HR, and speed SHI or SLO. Said at least two intervals t1, t2 of each measured variable should be different from said intervals present in the pulse groups of other variables or pulse group sequences formed by the pulse groups.

The system, formed in accordance with the present invention is a telemetric measuring system comprising one or more telemetric transmitter units 41 to 43, and at least two different sensors 41a to 43a in complete or partial connection with said one or more transmitter units 41 to 43 for measuring at least two different variables (HR, CAD, SHI, SLO). Thus, the system additionally comprises one telemetric receiver unit 44, to which the measurement results of the different sensors can be sent telemetrically by said one or more transmitter units 41 to 43. The system is characterized in that for each measured variable the system comprises a shaping element 41m, 42m, 43m for shaping the measured signal before telemetric transmission in such a way that a sequence, e.g. PGS(CAD), of pulse groups, e.g. PG(CAD), specific for each variable is generated on the basis of each measured signal. In the sequence of the variable, each pulse group comprises at least two intervals t1, t2, confined by at least three pulses, that differ from the intervals of the pulse groups of other variables. Similarly, the receiver unit 44 comprises an identifier part 45 by means of which the receiver identifies each measured variable based on the intervals of the pulse group. Such an identifier part 45 is in connection with a calculation unit 44e for calculating the values of different measured variables.

FIG. 4 shows that the shaping means are in connection with the transmission units. Each shaping means comprises at least two delay elements D(t1), D(t2) for forming a pulse group including the desired intervals t1, t2 on the basis of the measured signal. It is evident that the magnitudes of the delays determined by the delay elements differ one from another between the shaping units.

The measuring and transmitter units 41 to 43 operate in such a way that on the basis of the signal given by sensors 41a, 42a, 42c, respectively, the transmission pulse groups PG(HR), PG(SLO) or PH(SHI), PG(CAD), respectively, are shaped in the control unit 41c, 42c, 43c, respectively, preferably in the shaping units 41m, 42m, 43m, respectively, such that they comply with FIG. 5. FIG. 6 illustrates the operation of a shaping unit, e.g. the shaping unit 41m. In FIG. 6, the shaping unit 41m comprises delay elements D(t1) and D(t2), and an OR logic circuit 90. The measurement result of a variable is fed to all three blocks, i.e. to both delay circuits and to the OR circuit 90. The delay elements form delays of the length t1 and t2, whereby output OUT supplies pulse groups of the type described in FIG. 5.

In FIG. 3 the receiver unit 44 comprises an inductive receiver element 44a, a signal shaping element 44b, such as an amplifier 44b, detection means 44c, an interval identifier part 45, a control unit, or calculation unit 44e, and, if needed, a memory 44f and a display 44g. The detection means 44c can be implemented e.g. as a combination of an envelope sensor and a comparator. From the point of view of the invention, the most essential block in the receiver unit 44 is the identifier part 45. The identifier part interprets the total sequence formed as the sum of the pulse groups of different variables and uses the total sequence to detect the variable concerned. Based on the detected variable, the identifier part provides information to the control or the calculation unit 44e. The control unit, i.e. the calculation unit 44e, calculates the values of each variable based on the information received from the identifier part 45. The values of the variables may be stored in the memory 44f and/or shown on the display 44g. The identifier part 44 comprises e.g. a transfer register 144 and a plurality of collector elements 151 to 154. The transfer register comprises e.g. D flip-flops Q1 to Q38, each flip-flop operating in such a way that the flip-flop supplies to its output what it receives in its input, i.e. if the flip-flop input value is "1", it issues the state "1" as the output. The same applies to the state "0". The transfer register 144 comprises a clock control CLK for the flip-flops. The transfer register 144 is filled with received signal at a pace given by the clock CLK. If one of the pulse groups PG(HR), PG(SLO) or PG(SHI), PG(CAD), respectively, of FIG. 5 is present in the signal received by the receiver 44, the control unit sees it in the collector elements 151 to 154. Each variable HR, SHI, SLO, CAD has its own collector circuit.

Thus, the invention relates to a telemetric measuring method in accordance with an embodiment of which three different measured variables, i.e. heartbeat, speed and pedalling cadence of a bicycle, are measured by different sensors, and the measurement data on each measured variable is transferred by telemetric data transmission to the same receiver unit 44. In the invention, telemetric data transmission to the receiver unit 44 is carried out in such a way that the transmission pulse groups included in the measurement data represents a single measured variable comprise, in the transmission pulse group, at least two such intervals, formed between at least three identifier pulses. The combination of the intervals is specific to that particular measured variable, whereby, for identification of the different measured variables, the interval combination of the transmission pulse group of the measured variable concerned differs from the interval combinations that other measured variables show in their specific pulse groups or in a specific pulse group sequence formed by their pulse groups. Once the receiver unit 44 detects that an interval combination according to said at least two intervals is present in a common received pulse train, the transmission pulse group is identified as a transmission pulse group concerning a given measured variable, i.e. heartbeat, bicycle speed or pedalling cadence. A value for each measured variable, e.g. heartbeat, bicycle speed or pedalling cadence, is determined for the different measured varables, i.e. heartbeat, bicycle speed and pedalling cadence, on the basis of one or more transmission pulse groups identified in the above manner.

The solution in a preferred embodiment of the invention is such that said at least two intervals $t1$, $t2$ present in the transmission pulse group, e.g. PG(CAD), of a single measured variable, e.g. cadence CAD, have been selected in such a way that intervals of the same length do not appear in the transmission pulse groups PG(HR), PG(SLO) or PG(SHI) of the other measured variables, e.g. heartbeat HR, and speed SLO or SHI, or in the transmission pulse group sequences PGS(HR), PGS(SLO) or PGS(SHI) specific to the measured variables and formed by the transmission pulse groups of the other single measured variables, i.e. heartbeat or speed. This can be seen from FIG. 5, in which the intervals $t1$, $t2$ of the different measured variables have different lengths. According to the observations made by the applicant, a suitable length for the intervals $t1$ is between 10 and 50 ms. Similarly, according to the observations made by the applicant, a suitable length for the intervals $t2$ is between 50 and 250 ms. According to the observations of the applicant, a difference of about 5 to 20 ms is sufficient to make the lengths of the intervals of the different variables sufficiently different. The difference in length between intervals $t1$ and $t2$, in turn, is great. The difference in length between the intervals $t1$ of the different variables is slight. Similarly, the difference in length between the intervals $t2$ of the different variables is slight. The preferred embodiments ensure that the different variables are distinguishable one from another.

When considering the difference in length between the intervals $t2$, FIG. 5 shows, however, that in some variable, i.e. heartbeat HR, the interval $t2$ may be notably shorter than that of the other variables. This is due to the fact that in the preferred embodiment a user identifier code has been coded in the interval of said variable HR, i.e. the length of the interval $t2$ in said variable HR, i.e. heartbeat depends on the person concerned. The preferred embodiment increases the reliability of the measurement in a simple manner.

In a preferred embodiment of the invention, one or more transmitter units transmit pulse groups at intervals proportional to the frequency of occurrence of a measured variable, the receiver determining the result of the measured variable based on the interval between the pulse groups. The interval tg between successive pulse groups PG (CAD) of cadence CAD may serve as an example.

In another preferred embodiment of the invention, one or more transmitter units 41 to 43 transmit pulse groups that include, in addition to the two intervals described, at least one measuring value interval whose length is proportional to the value of the measured variable. In this case, the receiver determines the value of said measured variable based on said measuring value interval of the pulse group (not shown).

In a preferred embodiment of the invention, the lengths of the intervals $t1$, $t2$ have been selected such that the length of each interval $t1$, $t2$ is shorter than the estimated limit value, or minimum length of the interval, i.e. time period, comprising the variable to be measured, and/or longer than the maximum length of the interval comprising the value of the variable to be measured. Referring to heartbeat HR, said limit value, i.e. minimum length, is about 250 ms, corresponding to the highest imaginable pulse value 240 pulses/minute, i.e. 4 beats/second. This preferred embodiment prevents the interval comprising the measuring value (the interval tg between the pulse groups or some third interval between the pulses inside the pulse group) from disturbing the measurement.

In the preferred embodiment of the invention, a dedicated transmitter unit 41 to 43 is used for each measured variable in transferring the measurement data to the same receiver 44. This simplifies equipment implementation and the operation of the method.

In some cases, it is advantageous to use a common transmitter unit for transferring the measurement data for at least two different measured variables to the same receiver. The solution of a preferred embodiment of the invention is such that a common transmitter unit is used for transferring the measurement results of heartbeat and some other variable measured from the body, preferably temperature. In FIG. 4, for example, the pulse transmitter belt could comprise a sensor measuring body temperature in the same entity. Said solution reduces the number of transmitter units.

The method of the invention includes transferring the measurement data for each measured variable HR, CAD, SLO (or SHI) to the receiver unit 44 in a transmission pulse group sequence specific to the measured variable and formed by successive pulse groups, and transferring the pulse group sequences of the different measured variables HR, CAD, SLO (or SHI) as a total sequence to a receiver in a telemetric data transmission.

In the preferred embodiment of the invention, the measuring frequency of one or more measured variables, e.g. speed, is changed (by the divider 42g), and at the same time the combination formed by said at least two intervals $t1$, $t2$ of the transmission pulse group of the measured variable concerned is changed. The sensor part 45 of the receiver 44 detects the change in the combination formed by said intervals, and, based on this information, the receiver 44 changes the measuring value so that it corresponds to the actual measuring value, i.e. removes the influence of the divider 42g. Relating to this, the measuring frequency of a measured variable, particularly speed, and the pulse group intervals are preferably changed automatically once the measuring value exceeds a given value or falls below a given value.

The method of the invention is applicable to a personal telemetry measuring device, e.g. a pulse meter.

In addition to the above cycling application, the invention is also applicable to watercrafts, the measured variables being, e.g. a person's heartbeat, the speed and operating cadence of the watercraft, (such as the paddling or rowing cadence). In addition, the invention may be applied where a significant part of the measured variables, if not all, are measurements concerning the human body, such as two or more of the following: heartbeat, blood pressure, temperature, blood glucose content, and blood oxygen content.

The minimum number of measured variables is preferably two, and they can be selected in accordance with the application and the measuring needs.

Although the invention has been explained above with reference to examples in accordance with the accompanying

What is claimed is:

1. A telemetric measuring method, the method comprising the steps of:

measuring a value of at least one of a plurality of variables, the value of the variable being responsive to at least one of a bodily function and a bodily movement, the value of the at least one of the plurality of variables being measured by a sensor;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

2. A telemetric measuring method, the method comprising the steps of:

measuring a value of at least one of the plurality of variables, the value of the variable being responsive to at least one of a bodily function and a bodily movement, the value of the at least one of the plurality of variables being measured by a sensor, the at least one of the plurality of variables including at least one of a heartbeat rate, a bicycle speed, and a bicycle pedalling cadence;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one the plurality of variables from a duration of time between the at least two transmission pulse groups.

3. A telemetric measuring method, the method comprising the steps of:

measuring a value of at least one of the plurality of variables, the value of the variable being responsive to at least one of a bodily function and a bodily movement, the value of the at least one of the plurality of variables being measured by a sensor, the at least one of the plurality of variables including at least one of a heartbeat rate, a watercraft speed, and a watercraft operating cadence;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse group, the at least two transmission pulse groups being transmitted to a receiver;

transmission receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

4. A telemetric measuring method, the method comprising the steps of:

measuring a value of the at least one of the plurality of variables, the value of the variable being responsive to at least one of a bodily function and a bodily movement, the at least one of the plurality of variables being measured by a corresponding sensor, the at least one of the plurality of variables including at least one of a heartbeat rate, a blood pressure, a temperature, a blood glucose content, and a blood oxygen content;

generating at least two transmission pulse groups, the at least two transmission pulse groups being used to represent the value of the at least one of the plurality of variables, each of the at least two transmission pulse groups including at least two intervals and at least three pulses, the at least two intervals being separated by the at least three pulses, the at least one of the plurality of variables being identifiable by the at least two intervals;

transmitting the at least two transmission pulse groups, the at least two transmission pulse groups being transmitted to a receiver;

receiving the at least two transmission pulse groups, the at least two transmission pulse groups being received by the receiver;

identifying the at least one of the plurality of variables from the at least two intervals of at least one of the received at least two transmission pulse groups; and determining a value of the at least one of the plurality of variables from a duration of time between the at least two transmission pulse groups.

5. A telemetric measuring method as defined by claim 1, 2, 3, or 4, wherein the intervals are separated by the at least three pulses of different transmission pulse groups of the plurality of transmission pulse groups.

6. A telemetric measuring method as defined by claim 1, 2, 3, or 4, wherein a first combination of the at least two intervals is unequal to a second combination of at least two different intervals, a first variable of the plurality of variables being identifiable by the first combination, a second variable of the plurality of variables being identifiable by the second combination.

7. A telemetric measuring method as defined by claim 1, 2, 3, or 4, wherein the step of generating at least one transmission pulse group further includes the step of generating at least two transmission pulse groups separated by a duration of time proportional to the value of the at least one of the plurality of variables.

8. A telemetric measuring method as defined by claim 1, 2, 3, or 4, wherein the at least two intervals are at least one of less than the value of the plurality of variables and greater than the value of the plurality of variables.

9. A telemetric measuring method as defined by claim 1, 2, 3, or 4, wherein the at least one transmission pulse group is transmitted by a dedicated transmitter, the dedicated transmitter transmitting only transmission pulse groups being used to represent the value of the at least one of the plurality of variables.

10. A telemetric measuring method as defined by claim 1, 2, 3, or 4, wherein the at least one transmission pulse group is transmitted by a common transmitter, the common transmitter transmitting transmission pulse groups being used to represent the values of at least two of the plurality of variables.

11. A telemetric measuring method as defined by claim 1, 2, 3, or 4, wherein the at least one transmission pulse group is transmitted by a common transmitter, the common transmitter transmitting transmission pulse groups representative of a heartbeat rate and at least one other bodily variable.

12. A telemetric measuring method as defined by claim 1, 2, 3, or 4, wherein the step of transmitting the at least one transmission pulse group further includes the step of transmitting at least two transmission pulse groups as a transmission pulse group sequence, the transmission pulse group sequence being representative of the at least one of the plurality of variables.

13. A telemetric measuring method as defined by claim 1, 2, 3, or 4, wherein the step of measuring the at least one of the plurality of variables further includes the step of changing a frequency at which at least one of the plurality of variables is measured, wherein the step of generating the at least two transmission pulse groups further includes the step of changing at least one of the at least two intervals in response to changing the frequency, the change in the at least one of the at least two intervals being representative of the change in the frequency of measuring, wherein the step of determining the value of the at least one of the plurality of variables further includes the steps of detecting the change in the at least one of the at least two intervals and adjusting the value of the at least one of the plurality of variables in response to the change in the at least one of the at least two intervals.

14. A telemetric measuring method as defined by claim 13, wherein the step of changing the frequency at which at least one of the plurality of variables is measured further includes the step of automatically changing the frequency at which at least one of the plurality of variables is measured in response to the value of the at least one of the plurality of variables being one of greater than and less than a first value, wherein the step of changing the at least two intervals in response to changing the frequency further includes the step of automatically changing the at least one of the at least two intervals in response to the value of the at least one of the plurality of variables being one of greater than and less than the first value.

15. A telemetric measuring method as defined by claim 13, wherein the at least one of the plurality of variables includes speed.

16. A telemetric measuring method as defined by claim 1, 2, 3, or 4, wherein the at least two intervals are successive.

17. A telemetric measuring method as defined by claim 1, 2, 3, or 4, wherein at least one of the at least two intervals is representative of an identity of a user.

18. A telemetric measuring method as defined by claim 17, wherein the at least one of the plurality of variables includes a heartbeat rate of the user.

19. A telemetric measuring method as defined by claim 1, 2, 3, or 4, wherein the method is used in a personal telemetry-measuring device.

20. A telemetric measurement system, the telemetric measurement system comprising:

a plurality of sensors, each of the plurality of sensors measuring a value of at least one of a plurality of variables, the value of the variable being responsive to at least one of a bodily function and a bodily movement;

a plurality of shaping circuits, each of the plurality of shaping circuits being responsive to at least one of the plurality of sensors, the plurality of shaping circuits generating at least two transmission pulse groups, the at least two transmission pulse groups being used to represent the value of the at least one of the plurality of variables, at least one of the at least two transmission pulse groups including at least two intervals and at least three pulses, the at least two intervals being separated by the at least three pulses, the at least one of the plurality of variables being identifiable by the at least two intervals;

at least one transmitter, the at least one transmitter transmitting the at least two transmission pulse groups;

a receiver, the receiver receiving being responsive to the at least two transmission pulse groups;

an identifying circuit, the identifying circuit being responsive to the at least two transmission pulse groups, the identifying circuit identifying the at least one of the plurality of variables from the at least two intervals of at least one of the received at least two transmission pulse groups; and a calculating circuit, the calculating circuit determining the value of the at least one of the plurality of variables from a duration of time between the received at least two transmission pulse groups.

21. A telemetric measurement system as defined by claim 20, wherein the plurality of shaping circuits are coupled to the at least one transmitter.

22. A telemetric measurement system as defined by claim 20, wherein each of the plurality of shaping circuits includes at least two delay elements, the at least two delay elements generating the at least two intervals.

23. A telemetric measurement system as defined by claim 20, wherein the sensor is able to change a frequency at which at least one of the plurality of variables is measured, wherein at least one of the plurality of shaping circuits is able to change at least one of the at least two intervals in response to the change in the frequency of measuring.

24. A telemetric measurement system as defined by claim 20, wherein the identifying circuit includes a transfer register, at least one of the received at least two transmission pulse groups being inputted to the transfer register.

25. A telemetric measurement system as defined by claim 20, wherein the plurality of sensors measures a heartbeat rate and at least one of a bicycle speed and a pedalling cadence.

26. A telemetric measurement system as defined by claim 20, wherein the plurality of sensors measures a heartbeat rate and at least one of a watercraft speed and an operating cadence.

27. A telemetric measurement system as defined by claim 20, wherein the system is used in a personal telemetry measuring device.

28. A telemetric measuring method as defined by claim 14, wherein the at least one of the plurality of variables includes speed.

* * * * *